United States Patent [19]
Mueller et al.

[11] Patent Number: 5,395,980
[45] Date of Patent: Mar. 7, 1995

[54] ISOBUTANE OXIDATION PROCESS

[75] Inventors: Mark A. Mueller, Austin; John R. Sanderson, Leander, both of Tex.

[73] Assignee: Texaco Chemical Inc., White Plains, N.Y.

[21] Appl. No.: 215,448

[22] Filed: Mar. 21, 1994

[51] Int. Cl.$^6$ .................. C07C 409/04; C07C 409/06
[52] U.S. Cl. ...................................... 568/573; 568/568; 568/569; 568/571; 568/910
[58] Field of Search ............... 568/568, 569, 571, 573, 568/910, 910.5

[56] References Cited

U.S. PATENT DOCUMENTS

| | | |
|---|---|---|
| 2,845,461 | 7/1958 | Winkler et al. ................. 568/571 |
| 3,478,108 | 11/1969 | Grane ............................. 568/571 |
| 3,907,902 | 9/1975 | Grane ............................. 568/571 |
| 4,404,406 | 9/1983 | Lutz et al. ...................... 568/571 |
| 5,220,075 | 6/1993 | Ember ............................. 568/573 |
| 5,243,083 | 9/1993 | Cowley et al. .................. 568/571 |
| 5,243,084 | 9/1993 | Cochran et al. ................. 568/571 |
| 5,334,771 | 8/1994 | Ember et al. ................... 568/573 |

*Primary Examiner*—Werren B. Lone
*Attorney, Agent, or Firm*—Kenneth R. Priem; James L. Bailey; Richard A. Morgan

[57] ABSTRACT

In the non-catalytic liquid phase oxidation of isobutane, it has been found that the reaction is initiated with 0.05 wt % to 0.08 wt % ditertiary butyl peroxide.

4 Claims, No Drawings

ISOBUTANE OXIDATION PROCESS

BACKGROUND OF THE INVENTION

1. Field of the Invention

The invention relates to the production of tertiary butyl hydroperoxide. More particularly, the invention relates to the liquid phase oxidation of isobutane with molecular oxygen to form tertiary butyl hydroperoxide. Most particularly, the invention relates to initiation of the oxidation reaction in the absence of catalyst.

2. Related Methods in the Field

Tertiary butyl hydroperoxide is a starting material and an intermediate in the production of commercial chemicals. Tertiary butyl hydroperoxide is used in combination with molybdenum containing catalysts to convert olefins to the corresponding epoxides. The epoxides are the monomer intermediates for polymeric materials.

Because of the commercial utility, improvements in the process to produce tertiary butyl hydroperoxide continue.

U.S. Pat. No. 2,845,461 to D. L. E. Winkler et al. teaches the non-catalytic, liquid phase oxidation of isobutane to form tertiary butyl hydroperoxide. The reaction is initiated with amounts of tertiary butyl hydroperoxide or ditertiary butyl peroxide.

U.S. Pat. No. 3,478,108 to H. R. Grane teaches the liquid phase oxidation of isobutane with molecular oxygen. The induction period for the reaction is reduced by adding a small quantity of hydroperoxide from the previous run.

U.S. Pat. No. 3,907,902 to H. R. Grane teaches a method of increasing the selectivity to tertiary butyl hydroperoxide in the liquid phase oxidation of isobutane. Selectivity is improved by the presence of small amounts of isopropyl alcohol, isobutyl alcohol and secondary butyl alcohol.

SUMMARY OF THE INVENTION

An improved method has been discovered for initiating the non-catalytic liquid phase oxidation of isobutane with molecular oxygen to produce tertiary butyl hydroperoxide. The reaction is carried out at an oxidation temperature of about 125° C. to 155° C. and an oxidation pressure of about 350 psia (24 atm) to 800 psia (55 atm).

In the improvement, an initial reaction mixture is formed comprising 50 wt % or more isobutane, 10 wt % or more tertiary butyl alcohol and 0.05 wt % to 0.5 wt % ditertiary butyl peroxide. Molecular oxygen is added at oxidation reaction pressure and the initial reaction mixture is heated to reaction initiation temperature of 135° C. to 155° C. As a result, a steady state reaction mixture containing 10 wt % or more tertiary butyl hydroperoxide is achieved in 2 hours to 5 hours.

DETAILED DESCRIPTION OF THE INVENTION

The liquid phase oxidation of isobutane may be carried out in a batch, semi-continuous or continuous reaction vessel. The reaction vessel effluent, comprising a portion of the steady state reaction mixture, is subjected to product separation. Product separation is carried out by distillation, extractive distillation, solvent extraction or any combination thereof. Tertiary butyl hydroperoxide is recovered as a separate product or more typically in a mixture with the oxidation reaction coproduct tertiary butyl alcohol. Unconverted isobutane is recycled to oxidation reaction vessel.

The reaction vessel is designed to facilitate the contacting of liquid isobutane with molecular oxygen and for removal of heat from the exothermic oxidation reaction.

The oxidation reaction is carried out in a reaction vessel with means for withdrawing heat from the exothermic reaction mixture. For larger reaction vessels heat withdrawal means comprises heat exchanger tubes providing a quench medium such as chilled, demineralized water. For smaller reaction vessels, heat withdrawing means comprises a jacket carrying the quench medium.

Means is provided for heating the initial reaction mixture from an initial temperature, e.g., ambient temperature, to the reaction initiation temperature of 135° C. to 155° C. This means typically comprises a heat exchanger. Isobutane is passed through the tube side and high pressure steam is provided to the jacket. The heat exchanger may be positioned in the recycle line. During start up, isobutane is circulated between the reaction vessel and the product separation means with heat applied to the recycled isobutane. Once the reaction is initiated heating is terminated. This reaction initiation is indicated by reactor thermocouples showing a reaction exotherm within the reactor. A steady state reaction mixture is rapidly established containing 10 wt % or more tertiary butyl hydroperoxide in 2 hours to 5 hours. It has been known heretofore to initiate the reaction with ditertiary butyl peroxide. It has been discovered surprisingly, that the reaction is initiated with 0.05 wt % to 0.1 wt %, preferably 0.05 wt % to 0.08 wt % ditertiary butyl peroxide. Accordingly, the requirement for larger amounts of initiator has been eliminated.

This invention is shown by way of Example.

EXAMPLE

An initial reaction mixture was made up comprising isobutane, tertiary butyl alcohol and ditertiary butyl peroxide. The reaction mixture was heated to reaction temperature. Pure oxygen was then introduced. The steady state reaction mixture was sampled and analyzed for composition. The results of three trials is reported as follows:

|  | Run 1 | Run 2 | Run 3 |
| --- | --- | --- | --- |
| Steady State |  |  |  |
| Reaction Temperature | 142° C. | 141° C. | 141° C. |
| Reaction Pressure | 500 psia | 510 psia | 510 psia |
| Initial Composition |  |  |  |
| isobutane | 70 wt % | 69.4 wt % | 69.9 wt % |
| t-butyl alcohol | 18.3 wt % | 29.8 wt % | 30.0 wt % |
| ditertiary butyl peroxide | 11.7 wt % | 0.08 wt % | 0.1 wt % |
| Steady State Composition |  |  |  |
| isobutane | 68.7 wt % | 73.0 wt % | 69.5 wt % |
| t-butyl alcohol | 13.8 wt % | 12.3 wt % | 13.2 wt % |
| tertiary butyl hydroperoxide | 15.6 wt % | 13.2 wt % | 15.9 wt % |

While particular embodiments of the invention have been described, it will be understood, of course, that the invention is not limited thereto since many modifications may be made, and it is, therefore, contemplated to cover by the appended claims any such modification as fall within the true spirit and scope of the invention.

What is claimed is:

1. Non-catalytic liquid phase oxidation of isobutane with molecular oxygen to produce tertiary butyl alcohol and tertiary butyl hydroperoxide, at an oxidation reaction temperature of about 125° C. to 155° C. and an oxidation reaction pressure of about 350 psia (24 atm) to 800 psia (55 atm), wherein the improvement comprises:

forming an initial reaction mixture comprising 50 wt % or more isobutane, 10 wt % or more tertiary butyl alcohol and 0.05 wt % to 0.5 wt % ditertiary butyl peroxide, adding molecular oxygen to the initial reaction mixture at the oxidation reaction pressure and heating to a reaction initiation temperature of 135° C. to 155° C., thereby forming a steady state reaction mixture containing 10 wt % or more tertiary butyl hydroperoxide in 2 hours to 5 hours.

2. The method of claim 1 wherein in the initial reaction mixture the amount of ditertiary butyl peroxide is 0.05 wt % to 0.1 wt %.

3. The method of claim 1 wherein the initial reaction mixture the amount of ditertiary butyl peroxide is 0.05 wt % to 0.08 wt %.

4. The method of claim 1 wherein in the initial reaction mixture the amount of ditertiary butyl peroxide is about 0.08 wt %.

* * * * *